United States Patent
Prestrelski

(10) Patent No.: US 9,138,479 B2
(45) Date of Patent: Sep. 22, 2015

(54) FORMULATIONS FOR THE TREATMENT OF DIABETES

(71) Applicant: XERIS PHARMACEUTICALS, INC., Austin, TX (US)

(72) Inventor: Steven Prestrelski, San Diego, CA (US)

(73) Assignee: Xeris Pharmaceuticals, Inc., Austin, TX (US)

( * ) Notice: Subject to any disclaimer, the term of this patent is extended or adjusted under 35 U.S.C. 154(b) by 0 days.

(21) Appl. No.: 14/354,848

(22) PCT Filed: Oct. 31, 2012

(86) PCT No.: PCT/US2012/062816
§ 371 (c)(1),
(2) Date: Jun. 23, 2014

(87) PCT Pub. No.: WO2013/067022
PCT Pub. Date: May 10, 2013

(65) Prior Publication Data
US 2014/0349926 A1    Nov. 27, 2014

Related U.S. Application Data

(60) Provisional application No. 61/553,388, filed on Oct. 31, 2011, provisional application No. 61/609,123, filed on Mar. 9, 2012.

(51) Int. Cl.
*A61K 38/28* (2006.01)
*C07K 14/62* (2006.01)
*A61P 3/10* (2006.01)
*A61K 47/20* (2006.01)
*A61K 9/00* (2006.01)
*A61K 9/19* (2006.01)
*A61K 9/14* (2006.01)
*A61K 38/22* (2006.01)

(52) U.S. Cl.
CPC .............. *A61K 47/20* (2013.01); *A61K 9/0019* (2013.01); *A61K 9/145* (2013.01); *A61K 9/19* (2013.01); *A61K 38/22* (2013.01); *A61K 38/28* (2013.01)

(58) Field of Classification Search
CPC ..... A61K 38/28; A61K 9/0019; A61K 9/145; A61K 38/22; A61K 47/20; A61K 9/19
See application file for complete search history.

(56) References Cited

U.S. PATENT DOCUMENTS

| | | | |
|---|---|---|---|
| 3,016,895 A | 1/1962 | Sein | 604/60 |
| 4,608,764 A | 9/1986 | Leuenberger | 34/295 |
| 4,848,094 A | 7/1989 | Davis et al. | 62/64 |
| 4,927,571 A | 5/1990 | Huang et al. | 264/4.3 |
| 5,031,336 A | 7/1991 | Diesner et al. | 34/287 |
| 5,092,843 A | 3/1992 | Monroe et al. | 604/138 |
| 5,208,998 A | 5/1993 | Oyler | 34/288 |
| 5,260,306 A | 11/1993 | Boardman et al. | 514/291 |
| 5,716,640 A | 2/1998 | Kamei et al. | 524/451 |
| 5,932,547 A | 8/1999 | Stevenson et al. | 514/10.3 |
| 5,977,082 A | 11/1999 | Gatti et al. | 514/34 |
| 6,001,336 A | 12/1999 | Gordon | 424/46 |
| 6,051,256 A | 4/2000 | Platz et al. | 424/489 |
| 6,199,297 B1 | 3/2001 | Wisniewski | 34/284 |
| 6,253,463 B1 | 7/2001 | Hansen | 34/362 |
| 6,264,990 B1 | 7/2001 | Knepp et al. | 424/499 |
| 6,290,991 B1 | 9/2001 | Roser et al. | 424/502 |
| 6,309,663 B1 | 10/2001 | Patel et al. | 424/450 |
| 6,331,310 B1 | 12/2001 | Roser et al. | 424/423 |
| 6,371,939 B2 | 4/2002 | Bergens et al. | 604/156 |
| 6,495,164 B1 | 12/2002 | Ramstack et al. | 424/489 |
| 6,667,061 B2 | 12/2003 | Ramstack et al. | 424/489 |
| 6,676,958 B2 | 1/2004 | Gerber | 424/434 |
| 6,730,328 B2 | 5/2004 | Maskiewicz et al. | 424/499 |
| 7,005,421 B2 | 2/2006 | Gatti et al. | 514/34 |
| 7,163,704 B2 | 1/2007 | Zhang | 424/725 |
| 7,259,225 B2 | 8/2007 | Song et al. | 528/272 |
| 7,314,636 B2 | 1/2008 | Caseres et al. | 424/426 |
| 7,371,406 B2 | 5/2008 | Rasstack et al. | 424/489 |
| 7,396,841 B2 | 7/2008 | Doen et al. | 514/338 |
| 7,442,832 B2 | 10/2008 | Gentile et al. | 562/460 |
| 7,498,312 B2 | 3/2009 | Cohen et al. | 514/36 |
| 7,582,311 B1 | 9/2009 | Cleland et al. | 424/489 |
| 7,604,822 B2 | 10/2009 | Ionascu | 424/725.1 |
| 7,651,703 B2 | 1/2010 | Cleland et al. | 424/489 |
| 7,915,229 B2 | 3/2011 | Cohen et al. | 514/36 |
| 8,110,209 B2 | 2/2012 | Prestrelski et al. | 424/423 |
| 2003/0026884 A1 | 2/2003 | Mantius et al. | 426/488 |
| 2003/0119825 A1 | 6/2003 | Folger et al. | 514/226.5 |
| 2003/0170289 A1 | 9/2003 | Chen et al. | 424/426 |
| 2003/0191157 A1 | 10/2003 | Doen et al. | 514/337 |

(Continued)

FOREIGN PATENT DOCUMENTS

| | | |
|---|---|---|
| EP | 0 916 347 | 5/1999 |
| EP | 1 502 589 | 2/2005 |

(Continued)

OTHER PUBLICATIONS

Human insulin, from http://www.ncbi.nlm.nih.gov/protein/AAA59172.1, p. 1, accessed Nov. 26, 2014.*
DMSO Facts, from http://www.theundergroundcure.com/dmso-facts.html, p. 1, accessed Nov. 26, 2014.*
Citric Acid, from http://www.boldsky.com/health/nutrition/2011/natural-citric-acid-sources-030811.html, pp. 1-3, accessed Nov. 26, 2014.*
Water, from http://www.biology-online.org/dictionary/Water, pp. 1-3, accessed Apr. 24, 2014.*
Engeloch et al, Stability of Screening Compounds in Wet DMSO, Journal of Biomolecular Screening, 2008, 13, pp. 999-1006.*

(Continued)

*Primary Examiner* — Julie Ha
*Assistant Examiner* — Li Ni Komatsu
(74) *Attorney, Agent, or Firm* — Norton Rose Fulbright US LLP

(57) ABSTRACT

Disclosed is a formulation for parenteral administration comprising insulin that comprises a pH memory between 1 to 4 or between 6 to 8 and an aprotic polar solvent, wherein the insulin is solubilized in the aprotic polar solvent, wherein the solubilized insulin comprises stable monomeric or dimeric forms of insulin or mixtures thereof, and wherein the water content of the formulation is equal to or less than 15% w/v.

34 Claims, 5 Drawing Sheets

(56) References Cited

U.S. PATENT DOCUMENTS

| | | | |
|---|---|---|---|
| 2004/0142043 A1 | 7/2004 | Maeda et al. | 524/499 |
| 2004/0176341 A1 | 9/2004 | Chou et al. | 514/179 |
| 2005/0019436 A1 | 1/2005 | Burch et al. | 424/760 |
| 2005/0069591 A1 | 3/2005 | Bernstein et al. | 424/489 |
| 2006/0160823 A1 | 7/2006 | Witchey-Lakshmanan et al. | |
| 2006/0211982 A1 | 9/2006 | Prestrelski et al. | 604/60 |
| 2007/0196416 A1 | 8/2007 | Li et al. | 424/422 |
| 2008/0096967 A1 | 4/2008 | Lopez et al. | 514/567 |
| 2008/0145383 A1 | 6/2008 | Zauner et al. | 424/208.1 |
| 2008/0200383 A1 | 8/2008 | Jennings et al. | 514/12 |
| 2008/0220069 A1 | 9/2008 | Allison | 424/489 |
| 2008/0226689 A1 | 9/2008 | Berry et al. | 424/423 |
| 2008/0248999 A1 | 10/2008 | Steiner | 514/1.1 |
| 2008/0260840 A1 | 10/2008 | Alessi et al. | 424/489 |
| 2008/0305161 A1 | 12/2008 | Shah et al. | 424/456 |
| 2009/0215883 A1 | 8/2009 | Bouzada et al. | 514/449 |
| 2009/0226530 A1 | 9/2009 | Lassner et al. | 424/497 |
| 2009/0233912 A1 | 9/2009 | Castile et al. | 514/220 |
| 2010/0098735 A1 | 4/2010 | Jain et al. | 424/422 |
| 2010/0120660 A1 | 5/2010 | Balschmidt et al. | 514/1.1 |
| 2012/0046225 A1 | 2/2012 | Prestrelski et al. | 514/6.8 |
| 2012/0232001 A1* | 9/2012 | Prestrelski et al. | 514/5.9 |

FOREIGN PATENT DOCUMENTS

| | | |
|---|---|---|
| EP | 2 060 268 | 5/2009 |
| GB | 2 119 248 | 11/1983 |
| WO | WO 91/16882 | 11/1991 |
| WO | WO 95/32730 | 12/1995 |
| WO | WO 96/09814 | 4/1996 |
| WO | WO 98/09613 | 3/1998 |
| WO | WO 98/16250 | 4/1998 |
| WO | WO 98/27963 | 7/1998 |
| WO | WO 00/16829 | 3/2000 |
| WO | WO 01/76682 | 10/2001 |
| WO | WO 01/78687 | 10/2001 |
| WO | WO 02/00137 | 1/2002 |
| WO | WO 02/49660 | 6/2002 |
| WO | WO 03/007782 | 1/2003 |
| WO | WO 03/041684 | 5/2003 |
| WO | WO 03/051398 | 6/2003 |
| WO | WO 2004/037242 | 5/2004 |
| WO | 2004/057939 | 7/2004 |
| WO | WO 2004/057959 | 7/2004 |
| WO | WO 2004/091666 | 10/2004 |
| WO | WO 2004/098643 | 11/2004 |
| WO | WO 2005/010079 | 2/2005 |
| WO | WO 2006/031376 | 3/2006 |
| WO | WO 2007/140312 | 12/2007 |
| WO | WO 2008/030469 | 3/2008 |
| WO | WO 2008/041245 | 4/2008 |
| WO | 2008/098212 | 8/2008 |
| WO | WO 2008/098212 | 8/2008 |
| WO | WO 2008/132224 | 11/2008 |
| WO | WO 2009/045837 | 4/2009 |
| WO | WO 2009/060473 | 5/2009 |
| WO | WO 2009/070298 | 6/2009 |
| WO | WO 2010/018596 | 2/2010 |
| WO | WO 2011/154725 | 12/2011 |
| WO | WO 2012/012460 | 1/2012 |
| WO | WO 2012/122535 | 9/2012 |

OTHER PUBLICATIONS

Brown, Clinicians' Guide to Diabetes Gadgets and Gizmos, Clinical Diabetes, 2008, 26, pp. 66-71.*

Amylin Agonists, from http://www.globalrph.com/amylin-agonists.htm, pp. 1-5, accessed Nov. 30, 2014.*

Anderson et al., "Revised estimate of the prevalence of multiple sclerosis in the United States", Ann. Neruol, 31(3):333-336, 1992.

Arnon and Aharoni, "Neurogenesis and neuroprotection in the CNS—fundamental elements in the effect of Glatiramer acetate on treatment of autoimmune neurological disorders ", Mol. Neurobiol., 36:245-253, 2007.

Bjartmar and Fox, "Pathological mechanisms and disease progression of multiple sclerosis: therapeutic implications", Drugs of Today, 38:17-29, 2002.

Bornstein et al., "A pilot trial of Cop 1 in exacerbateing remitting multiple sclerosis", New Eng. J. Med., 317:408-414,1987.

Bornstein et al., "A placebo-controlled, double-blind, randomized, two-center, pilot trial of Cop-1 in chronic progressive multiple sclerosis", Neurology, 41:533-539, 1991.

Bromberg, L. et al., "Transport of proteins dissolved in organic solvents across biomimetic membranes," *Proceedings of the National Academy of Sciences* 92(5): 1262-1266, 1995.

Buffer Reference Center, from http;//www.sigmaaldrich.com/, pp. 1-7, accessed Jul. 3, 2013.

Cervera et al, "Mechanism of action of exenatide to reduce postprandial hyperglycemia in type 2 diabetes", Am. J. Physiol. Endocrinol. Metab., 294:E846-E852, 2008.

Chang and Hershenson, "Practical Approaches to Protein Formulation Development", In: *Rationale Design of stable protein formulations—theory and practice*, pp. 1-25, 2002.

Chang et al., "Development of a Stable Freeze-dried formulation of Recombinant Human Interleukin-1 Receptor Antagonist", *Pharmaceutical Research*, 13(2):243-249, 1996.

Comi & Filippi, "Treatment with glatiramer acetate delays conversion to clinically definiate multiple sclerosis (CDMS) in patients with clinically isolated syndromes (CIS)", Neurology, 71(2):153, 2008.

Comi et al, "Results from a phase III, one-year, randomized, double-blind, parallel-group, dosecomparison study with glatiramer acetate in relapsing-remitting multiple sclerosis", Mult. Scler., 14(suppl. 1):S299, 2008.

Comi et al., "European/Canadian multicener, double-blind, randomized, placebo-controlled study of the effects of glatiramer acetate on magnetic resonance imaging-measured disease activity and burden in patents with relapsing multiple sclerosis", Ann. Neurol., 49:290-297, 2001.

Compston et al., "The Story of Multiple Sclerosis" In: McAlpine's Multiple Sclerosis. London: Churchill Livingston, pp. 3-42, 2006.

Definition of analog, from http://cancerweb.ncl.ac.uk/cgi-bin/omd?query=analog, pp. 1-5, accessed Jul. 7, 2005.

DeLuca, "Freeze drying of pharmaceuticals", J. Vac. Sci. Technol., 14(1):620, 1977.

Dhib-Jalbut, "Glatirmaer acetate (Copaxone) therapy for multiple sclerosis", Pharmacol Ther., 98:245-255,, 2003.

Dhib-Jalbut, "Mechanisms of action of interferons and glatiramer acetate in multiple sclerosis", Neurology, 25 58(Suppl 4):S3-S9, 2002.

Encyclopedia of Pharmaceutical Technology, vol. 6, Suspensions, pp. 3597-3610, 2007.

European Search Report for EP Appl. No. EP 12180169.0 dated Oct. 25, 2012.

Fleming and Carrithers, "Diagnosis and management of multiple sclerosis", Professional communications, Inc., 4 pages, 2002.

Geary and Smith, "Pancreatic Glucagon Fails to Inhibit Sham Feeding in the Rat", Peptides, 1:163-166, 1982.

Guideline on clinical investigation of medicinal products for the treatment of multiple sclerosis EMEA, London Sep. 16, 2006.

International Search Report and Written Opinion issued in PCT Application PCT/US2013/048293, dated Aug. 8, 2013.

International Search Report and Written Opinion issued in PCT Application PCT/US2011/044576, dated Dec. 14, 2011.

International Search Report and Written Opinion issued in PCT Application PCT/US2012/028621, dated Aug. 22, 2012.

International Search Report and Written Opinion issued in PCT Application PCT/US2012/062816, dated Jan. 31, 2013.

Johnson et al., "Extended use of glatiramer acetate (Copaxone) is well tolerated and maintains its clinical effect on multiple sclerosis relapse rate and degree of disability", Neurology, 50:701-708, 1998.

Kansara et al., "Subcutaneous delivery", Drug. Deliv. Technol, 9(6):38-42, 2009.

Meyer et al., "Preparation and in vitro characterization of gentamycin-impregnated biodegradable beads suitable for treatment of osteomyelitis ", Journal of Pharmaceutical Sciences, 87(9):1149-1154, 1998.

Noseworthy et al, "Multiple sclerosis", New Engl. J. Med., 343:938-952, 2000.

(56) References Cited

OTHER PUBLICATIONS

Ruggiere et al., "Glatiramer acetate in multiple sclerosis: A review", CNS Drug Reviews, 13(2):178-191, 2007.
Rubiono, *Solubilization of Some Poorly Soluble Drug by cosolvents, PhD dissertation*, The University of Arizona, 1984.
Shire et al., "Challenges in the development of high protein concentration formulations", J. Pharm. Sci., 93(6):1390-1402, 2004.
Tselis et al., "Glatiramer acetate in the treatment of multiple sclerosis", Neuropsychiatric Dis. Treat. 5Q, 3(2):259-267, 2007.
Wang, "Lyophilization and development of solid protein pharmaceuticals", *International Journal of Pharmaceutics*, 203:1-60, 2000.
Weber et al., "Mechanism of action of glatiramer acetate in treatment of multiple sclerosis", *Neurotherapeutics*, 4(4):647-653, 2007.
Williams and Polli, "The lyophilization of pharmaceuticals: a literature review", *Journal of Parenteral Science and Technology*, 38(2), 1984.
Wolinsky et al, "Glatiramer acetate in primary progressive multiple sclerosis: Results of a multinationa, multicener, double-blind, placebo-controlled trial", Ann Neurool, 61:14-24, 2007.
Wolinsky, "The use of glatiramer acetate in the treatment of multiple sclerosis", Adv. Neurol., pp. 273-292, 2006.
Zacharis et al., "Volatile buffers can override the 'pH memory' of subtilisin catalysis in organic media", Proc. Natl. Acad. Sci. USA, 96:1201-1205, 1999.
Ziemssen and Schrempf, "Glatiramer acetate: Mechanisms of action in multiple sclerosis", International Rev. of Neurobiol., 79:537-570, 2007.
Administer Intramuscular, Subcutaneous, and Intradermal Injections, from http://www.brooksidepress.org/Products/Administer_IM_SQ_and_ID_Injections/lesson_1 . . . , pp. 1-3, published on 2007.
Buffer Reference Center, from http://sigmaaldrich.com/life-science/core-bioreagents/biological-buffers/learningcenter. Accessed Jul. 3, 2013.
Carpenter, et al., "Rational Design of Stable Lyophilized Protein Formulations: Theory and Practice." pp. 1-25. 2002.
Definition of mimetic, from http://www.merriam-webster.com/medical/mimetic, p. 1, accessed Jun. 26, 2014.
Diabetes Mellitus-Merck Manual, from http://www.merckmanuals.com/professional/print!endocrine_and_metabolic_disorders/diab . . . , pp. 1-22, accessed Apr. 2, 2013.
Glossary of medical education terms, Institute of International Medical Education. http://www.iime.org/glossary.htm. Accessed in Mar. 2013.
Hypoglycemia-Merck Manual, from http://web.archive.org/web/20120115004118/http://www.merckmanuals.com/professional/ pp. 1-2, published on May 2007.
Iasemidis LD, "Epileptic Seizure Prediction and Control." IEEE Transac Biomed Eng. 50:549-558. 2003.
Izutsu, Stabilization of Therapeutic Proteins by Chemical and Physical Methods, pp. 287-292, from Therapeutic Proteins Methods and Protocols, Edited by C. Mark Smales and David C. James, published on 2005.
Autret, E. et al.: "Double-blind, randomized trial of diazepam versus placebo for prevention of recurrence of febrile seizures", *The Journal of Pediatrics*, vol. 117, No. 3, Sep. 1990, p. 490-494.
Knudsen, F Ursin; "Recurrence risk after first febrile seizure and effect of short term diazepam prophylaxis", *Archives of Disease in Childhood*, vol. 60, 1985 p. 1045-1049.
Pellock, John et al.: *Pediatric Epilepsy: Diagnosis and Therapy: Third Edition*—Chapter 19 "Febrile Seizures", 2008, p. 293-301.

\* cited by examiner

FORMULATIONS FOR THE TREATMENT OF DIABETES

CROSS REFERENCE TO RELATED APPLICATIONS

This application claims the benefit of U.S. Provisional Application No. 61/609,123, filed Mar. 9, 2012, and U.S. Provisional Application No. 61/553,388, filed Oct. 31, 2011. The contents of the above-referenced applications are incorporated into this application by reference.

BACKGROUND OF THE INVENTION

A. Field of the Invention

The invention concerns insulin formulations for parenteral administration. These formulations can include stable monomer and dimeric forms of insulin, thereby speeding up the absorption rate of insulin into a subject's blood stream.

B. Description of Related Art

Patients with Type 1 diabetes produce little to no insulin, and thus the primary treatment for Type 1 diabetes is exogenous insulin therapy. Further, due to limitations of non-insulin treatments, many patients with Type 2 diabetes eventually require insulin therapy. Historically, insulin has been used for more than 90 years to treat diabetes. A typical regimen involves administering several injections of insulin each day: a long-acting basal insulin one or two times per day and a rapid-acting insulin at mealtimes. Although this treatment regimen is accepted as effective, it has limitations. First, patients generally dislike injecting themselves with insulin due to the inconvenience and pain of needles. As a result, patients tend not to comply adequately with the prescribed treatment regimens. More importantly, even when properly administered, no meal-time injectable insulin products adequately replicate the natural physiologic action of human insulin. In particular, the first-phase response in a non-diabetic consists of an insulin spike with the insulin level in the blood rising within several minutes of the entry of glucose into the blood from a meal. The insulin level in the blood will then peak between 30 and 60 minutes after the onset of action. In contrast, injected insulin enters the blood slowly, with the observed maximum concentration (Cmax) occurring 90 minutes or more following the injection of regular human insulin.

Various classes of therapeutic insulin and insulin analogues have been developed to achieve different pharmacokinetic (PK) profiles such as trading-off onset of action and time-to-peak plasma insulin with duration-of-action. A key improvement in insulin treatments was the introduction of rapid-acting insulin analogs, including HUMALOG®, NOVOLOG® and APIDRA®. However, even with these analogs, peak insulin levels typically occur ~60 minutes following injection. The failure of currently marketed insulin products to adequately mimic the first-phase insulin release results in deficient insulin levels at the beginning of a meal and excessive insulin levels between meals, which can have the physiological effect of hyperglycemia early after meal onset and hypoglycemia late after meals. Both of these situations represent significant challenges to the promise of a closed-loop artificial pancreas technology in that complex algorithms are required to manage both latencies.

For diabetic patients treated with insulin, the primary route of administration of exogenous insulin is subcutaneous, and the primary parameters of the PK profile are dependent on subcutaneous absorption. A number of variables affect the absorption of subcutaneously injected insulin (e.g., blood flow, diffusion rates, and association state). When blood flow rates are sufficient, the rate-limiting factors for absorption of soluble insulin are (i) interstitial transport to the capillaries by diffusion and (ii) the restriction of transport over the capillary membrane both of which are governed by the size of the molecule (i.e., association state of insulin).

Typically, insulin formulations are aqueous-based. One reason for this is that the majority of the human body is made up of water, including blood plasma, which is an aqueous environment. Therefore, there is a natural tendency to administer a drug formulation that is compatible with the environment that the drug is intended to reach. While monomeric and dimeric insulin forms are more easily absorbed into the blood stream due to their smaller sizes when compared with the hexamer form of insulin, insulin is generally present in pharmaceutical compositions in the form of stabilized, zinc-bound hexamers. Monomeric insulin in aqueous solution is unstable, forming amyloid fibrils and degrading through water-mediated pathways. While the hexamer structure promotes stability in solution (pH 5-8), it also hinders diffusion and subsequent absorption. Further, the volume of the injection depot will also have an effect on diffusion, so that the larger the volume, the slower the diffusion rate. It is this combination of factors that is primarily responsible for the latency in onset of action and peak plasma insulin levels.

To prevent fibrillation and degradation of insulin in aqueous solution while also promoting subcutaneous absorption, insulin analogs have been developed where the amino acid sequence has been changed to reduce the propensity for self-association while preserving receptor-binding affinity. These classes of insulin are often referred to as "monomeric" insulin, but they actually exist as weakly associated hexamers. Absorption of such preparations will still be delayed because it is dependent on the diffusion and subsequent reduction in subcutaneous concentration required for the hexamer to dissociate to the dimer/monomer. Insulin analogs with equilibrium in favor of the monomeric state (e.g. the insulin analog Lispro) have shown more rapid absorption and a shorter duration of action. However, these analog molecules are less stable and more prone to irreversible aggregation under thermal and mechanical stress compared to hexameric insulin. Moreover, these aggregates decrease not only the dose of insulin available, but can also induce irritation or immune reactions in patients. Concerns also have emerged in experimental and epidemiological studies with respect to prolonged signaling of the receptor machinery and the induction of tumor proliferation by some newer insulin analogs. Despite their shortfalls, insulin analogs are costly—about twice as much as regular human insulin.

SUMMARY OF THE INVENTION

The present invention provides a solution to the current problems facing insulin formulations. The invention resides in drying insulin in a buffer to create a dried form of insulin that maintains a desired pH after it is reconstituted and solubilized in an aprotic polar solvent. The resulting formulation includes solubilized and stabilized monomeric and dimeric forms of insulin. Notably, the formulations can have relatively low amounts of water (20, 15, 10, 5, 4, 3, 2, 1, % or less) or can be non-aqueous, which further allows for increased amounts of insulin to be present in the formulation, thereby reducing the volume of the insulin containing formulation to be administered to a subject. Further, the invention allows for both non-modified or native and modified or analogue forms of insulin to be used. Stated another way, while insulin analogs can be used with the present invention, non-modified/ native insulin can also be used and remain stable in both its monomeric and dimeric forms.

In one aspect of the present invention, there is disclosed a formulation comprising insulin that has a pH memory between 1 to 4 (or 1 to 3 or about 2) or between 6 to 8 (or 6.5 to 7.5 or about 7) and an aprotic polar solvent, wherein the insulin can be solubilized in the aprotic polar solvent, wherein the solubilized insulin can include stable monomeric or dimeric forms of insulin or mixtures thereof, and wherein the water content of the formulation can be equal to or less than 20, 15, 10, 5, 4, 3, 2, 1% w/v or w/w or less (e.g., anhydrous). The formulation can be used for parenteral administration. In certain aspects, the aprotic polar solvent can be dimethylsulfoxide (DMSO), n-methyl pyrrolidone (NMP), ethyl acetate, dimethylformamide (DMF), dimethylacetamide (DMA), or propylene carbonate, or mixtures thereof. In certain aspects, the aprotic polar solvent can be dimethylsulfoxide (DMSO). In some aspects, the formulation comprises 3 mg/ml to 50 mg/ml, 3 mg/ml to 10 mg/ml, or 10 mg/ml to 50 mg/ml of insulin. In others, it can include 0.5, 1, 2, 3, 4, 5, 6, 7, 8, 9, 10, 15, 20, 25, 30, 35, 40, 45, 50, 55, 60, 65, 70, 75, 80, 90, 100 mg/mL, or more or as needed, or any range therein. In some aspects, the majority of the insulin within the formulation is monomeric form or dimeric form or a combination of monomeric and dimeric forms. The formulation can further include ingredients that are capable of reducing the aggregation of monomeric or dimeric forms of insulin. Non-limiting examples of such ingredients include urea, guanidinium chloride, an amino acid, a sugar, a polyol, a polymer, an acid, or a surfactant, or mixtures thereof. In certain aspects, the acid can be acetic acid, ascorbic acid, citric acid, glutamic acid, aspartic acid, succinic acid, fumaric acid, maleic acid, or adipic acid, or mixtures thereof. The formulation can include a co-solvent. One non-limiting example of a co-solvent is water. In some aspects, the formulation does not include zinc, includes low amounts of zinc and/or includes zinc that is bound to a chelating agent so as to reducing the likelihood of hexamer formation. In certain aspects, the insulin can be previously dried in a non-volatile buffer, said buffer can have a pH range between 1 to 4 or between 1 to 3 or about 2 or between 6 to 8 or 6.5 to 7.5 or about 7. Examples of non-volatile buffers can be a glycine buffer, a citrate buffer, or a phosphate buffer, or mixtures thereof. In some aspects, the buffer can include a chelating agent. Non-limiting examples of chelating agents include ethylenediaminetetraacetic acid (EDTA), ethylene glycol tetraacetic acid (EGTA), tartaric acid, glycerin, or citric acid or any combination thereof. The formulation can also include an ingredient that is capable of depressing the freezing point of the aprotic polar solvent to about 0° C., and non-limiting examples of such an ingredient include water, a sugar, a sugar alcohol, or mixtures thereof. In some instances, the insulin can be non-modified or native human insulin. In other aspects, the composition can further include an insulin adjuvant such as an amylin analog. The amylin analog can be solubilized in the formulation. A non-limiting example of an amylin analog is pramlintide. The pramlintide can be processed such that it has a pH memory between 1 to 5, or 2, 3, or 4, or about 2. In some particular instances of the co-formulation, the insulin pH memory can be about 2 and the pramlintide pH memory can be about 2. In some aspects, the processing of the pramlintide can include drying said pramlintide in a non-volatile buffer, said buffer having a pH range between 1 to 5, or 2, 3, or 4, or about 2. In formulations that include insulin and pramlintide, the water content can be between 5 to 20% w/v or w/w or 5 to 15% w/v or w/w or 7 to 12% w/v or w/w, or 8 to 10% w/v or w/w, or about 9% w/v or w/w. The formulation can be in liquid form. The formulation can be a solution. In certain aspects, least 50, 60, 70, 80, or 90% or more of the insulin within the formulation can remain chemically and physically stable when the formulation is stored at room temperature for one month. In some aspects, the formulation can be comprised within a container. The container can be a syringe, a pen injection device, an auto-injector device, a pump, or a perfusion bag. In certain aspects, the aprotic polar solvent can be the continuous phase of the formulation. The formulation can include at least 75, 80, 85, 90, 95, 96, 97, 98, 99 or % w/v or w/w of the aprotic polar solvent. The insulin within the formulation can be meta-stable.

Also disclosed is a method for reducing blood glucose level comprising administering to a subject in need thereof any one of the formulations of the present invention in an amount effective to reduce the blood glucose level in the subject. The subject can be human (adult or child), an animal (e.g., chimpanzee, horse, cow, pig, rabbit, rat, mouse, etc.). In certain aspects, the blood glucose level in the subject is reduced within 10, 20, 30 minutes, 60 minutes, or 90 minutes after administration. In some instances, the early ½ Tmax blood insulin level in the subject occurs within 10, 20, 30, 40, 50, or 60 minutes after administration or within 30 to 60 minutes after administration. The subject can have already been diagnosed with Type-I or Type-II diabetes or can be susceptible to developing Type-I or II diabetes. In some instances, the formulation can be administered within 30, 20, 15, 10 minutes, 5, minutes, or 1 minute before ingestion of food by the subject, or within 1 minutes, 5 minutes, 10, 15, 20, or 30 minutes after ingestion of food by the subject.

Also disclosed is a method of making the formulations of the present invention. The method can include drying a mixture comprising insulin and a non-volatile buffer to obtain dried insulin, wherein the dried insulin can have a pH memory between 1 to 4 (or 2 to 3 or about 2) or 6 to 8 (or 6.5 to 7.5 or about 7) and subsequently reconstituting the dried insulin in an aprotic polar solvent, wherein the insulin can be solubilized in the aprotic polar solvent, wherein the solubilized insulin can include stable monomeric or dimeric forms of insulin or mixtures thereof, and wherein the water content of the formulation can be equal to or less than 20, 15, 10, 5, 4, 3, 2, 1% w/v or w/w or less (e.g., anhydrous). The method can further include drying a mixture comprising an amylin analog and a second non-volatile buffer to obtain a dried amylin analog and reconstituting the dried amylin analog in the aprotic polar solvent along with the dried insulin, wherein the dried amylin analog can be solubilized in the aprotic polar solvent. As noted above, the amylin analog can be pramlintide and can be processed to have a pH memory between 1 to 5, or 2, 3, or 4, or in particular instances of about 2. In some particular instances of the co-formulation, the insulin pH memory can be about 2 and the pramlintide pH memory can be about 2. The second non-volatile buffer can have a pH range between 1 to 5 or about 2, 3, or 4, or more particularly about 2. This method can further include adding a co-solvent such as water to the formulation in amounts ranging from 5 to 20% w/v or w/w or 5 to 15% w/v or w/w or 7 to 12% w/v or w/w, or 8 to 10% w/v or w/w, or about 9% w/v or w/w.

Another unique aspect of the present formulation is that it can be contained in a container, be stored, and be immediately ready for parenteral administration on an as needed basis without having to reconstitute or dilute the formulation. Therefore, the container that the formulation can be stored in can be a syringe, a pen injection device, an auto-injector device, a pump, or a perfusion bag. Also contemplated for use in the formulations are additional ingredients/pharmaceutical excipients, non-limiting example of which include: antioxidants (examples include ascorbic acid, cysteine, methionine, monothioglycerol, sodium thiosulfate, sulfites, BHT, BHA, ascorbyl palmitate, propyl gallate, or vitamin E); chelating agents (examples include EDTA, EGTA, tartaric acid, glycerin, or citric acid); or preservatives (examples include alkyl alcohols, benzyl alcohol, a methyl paraben, or a propyl paraben or mixtures thereof). The formulation can be in liquid form, semi-solid form, or gel form. As discussed below, the formulation can have a desired viscosity range (in one non-limiting example, such a range could be between 0.5 to 15 cps).

It is contemplated that any embodiment discussed in this specification can be implemented with respect to any method or composition of the invention, and vice versa. Furthermore, compositions of the invention can be used to achieve methods of the invention.

"Insulin" means human, non-human, recombinant, purified, and/or synthetic (e.g., modified insulin or insulin analogs) insulin. "Human insulin" means the human peptide hormone insulin that is secreted by the pancreas—it can be isolated, from a natural source, made from a genetically altered organism, manufactured via synthetic chemistry, purchased, etc. "Non-human insulin" is insulin derived from an animal (e.g., pig, cow, etc.).

"Modified insulin" or "insulin analog" is an altered form of insulin, different from that in nature (e.g., chemical modification, different structure, different amino acid sequence), but still available to a subject (e.g., human) to perform the same function as natural/un-modified insulin. For instance, through genetic engineering of the coding of DNA, the amino acid sequence of insulin can be changed to alter its ADME (adsorption, distribution, metabolism, and/or excretion) characteristics. Examples of modified insulin or insulin analogs include Lispro, Aspart, Glulisine, Detemir, Degludec, etc. Unmodified or native insulin includes the native or naturally occurring amino acid sequence.

"Stable insulin" means insulin within the formulation does not irreversibly aggregate within the formulation or otherwise lose its activity once the formulation is administered. The insulin retains its activity once absorbed into the blood. Without wishing to be bound by theory, it is believed that the insulin within the formulation of the present invention is "meta-stable" in that while the conformation of the solubilized insulin may change, the insulin reverts back to its native conformation once administered and absorbed into the blood. Further, it is believed that the conformational change of insulin within the formulation reduces the likelihood of aggregation with other insulin monomers and dimers or adjuvants such as amylin analogs present within the formation. Monomeric insulin form means insulin in its monomer form. Dimeric insulin form means insulin in its dimeric form (e.g., two monomers associated or coupled together). Hexamer insulin form means insulin in its hexamer form (e.g., three dimeric forms associated or coupled together).

"Zinc-free" or "low-zinc" means that the formulation includes about 0.6% or less (e.g., 0.5, 0.4, 0.3, 0.2, 0.1, 0%) zinc relative to the insulin content or 3 zinc ions per 6 insulin monomers or less (e.g, 2, 1, 0).

"Aprotic polar solvent" means a polar solvent that does not contain acidic hydrogen and does not act as a hydrogen bond donor. As noted above, non-limiting examples include dimethylsulfoxide (DMSO), dimethylformamide (DMF), ethyl acetate, n-methyl pyrrolidone (NMP), dimethylacetamide (DMA) and propylene carbonate.

"Parenteral administration" refers to the administration of the formulation under or through one or more layers of skin or mucus membranes of an animal, such as a human. Standard parenteral administrations are given into the subcutaneous or intramuscular region of an animal, e.g., a human patient. These deep locations are targeted because the tissue expands more easily, relative to shallow dermal sites, to accommodate the injection volumes to deliver insulin formulations. Administration can be with a needle, pump, injection device, catheter, etc.

"Pharmaceutically acceptable carrier" means a pharmaceutically acceptable solvent, suspending agent or vehicle for delivering insulin to a mammal such as an animal or human.

"Pharmaceutically acceptable" ingredient, excipient or component is one that is suitable for use with humans and/or animals without undue adverse side effects (such as toxicity, irritation and allergic response) commensurate with a reasonable benefit/risk ratio.

"Biocompatible" means that it is suitable for use with human or animals without undue adverse side effects (such as toxicity, irritation, and allergic response) commensurate with a reasonable benefit/risk ratio.

"Bioavailability" refers to the extent to which the insulin is absorbed from the formulation by the subject.

"Systemic" means, with respect to delivery or administration of insulin to a subject, that therapeutic agent is detectable at a biologically significant level in the blood plasma of the subject.

"Patient," "subject," or "individual" refers to a mammal (e.g., human, primate, dog, cat, bovine, ovine, porcine, equine, mouse, rate, hamster, rabbit, or guinea pig).

"Inhibiting" or "reducing" or any variation of these terms, when used in the claims and/or the specification includes any measurable decrease or complete inhibition to achieve a desired result.

"Effective" or "treating" or "preventing" or any variation of these terms, when used in the claims and/or specification, means adequate to accomplish a desired, expected, or intended result.

The term "about" or "approximately" are defined as being close to as understood by one of ordinary skill in the art, and in one non-limiting embodiment the terms are defined to be within 10%, preferably within 5%, more preferably within 1%, and most preferably within 0.5%. Further, "substantially non-aqueous" refers to less than 5%, 4%, 3%, 2%, 1%, or less by weight or volume of water.

The use of the word "a" or "an" when used in conjunction with the term "comprising" in the claims and/or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the transitional phase "consisting essentially of," in one non-limiting aspect, a basic and novel characteristic of the formulations and methods disclosed in this specification includes the stability and solubility of the monomeric and/or dimeric forms of insulin within said formulations. Therefore, ingredients that can affect the stability or solubility of the monomeric and/or dimeric forms of insulin within the formulations would be excluded from said formulations in instances where a claim uses the transitional phrase "consisting essentially of."

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented below.

DESCRIPTION OF ILLUSTRATIVE EMBODIMENTS

Figure 1:
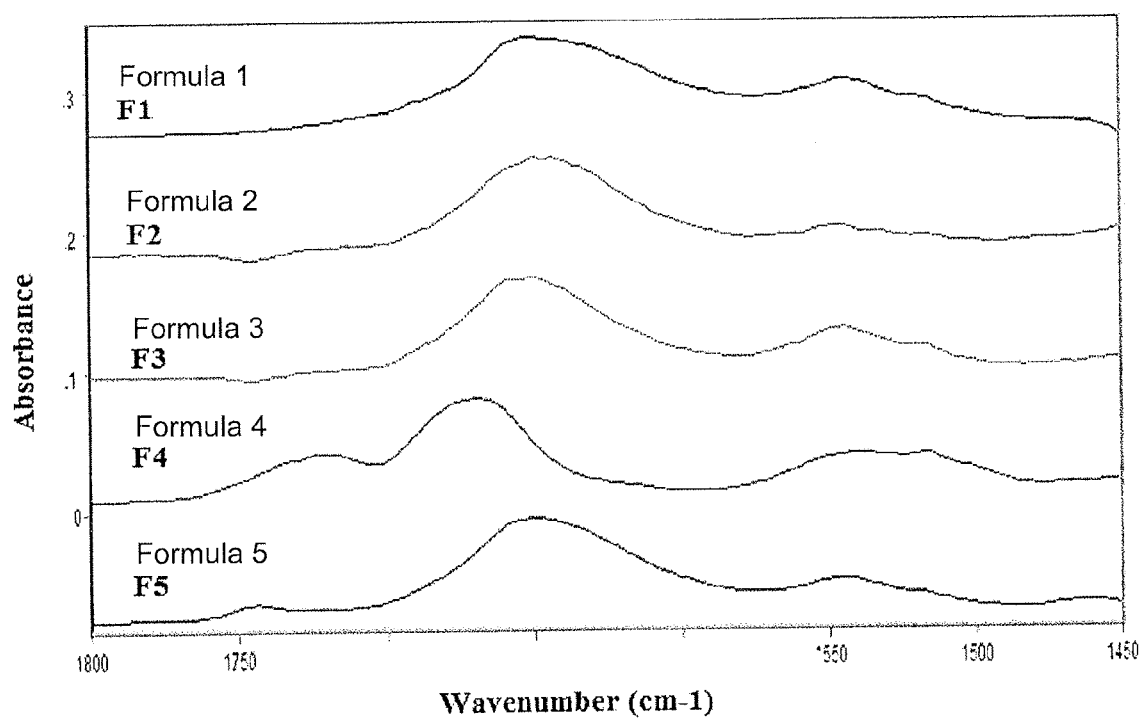
FIG. 1: the FTIR spectra of DMSO/Insulin and Aqueous/Insulin formulations.

As discussed above, the difficulties associated with formulating insulin in its monomeric or dimeric forms for parenteral administration are well-documented. The current solutions to such difficulties are also well-documented and accepted as standard practice in the formulations field. For instance, insulin analogs/modified insulin have been prepared to reduce its binding affinity with itself in hopes of avoiding hexamer formation of the analogs. These analogs are typically administered in an aqueous environment, which reduces their stability and makes them more prone to irreversible aggregation once aggregation occurs. Further, such analogs are costly and can induce irritation or immune reactions in patients.

By comparison, the inventors have found a solution to the aforementioned problems. The solution resides in preparing insulin that has a particular pH memory and reconstituting and solubilizing said insulin in an aprotic polar solvent. The resulting formulation, which can have low amounts of water to no water, includes solubilized and stabilized monomeric and dimeric forms of insulin. Further, the increased solubility of insulin in aprotic polar solvents results in a low volume formulation that has high amounts of monomeric and dimeric forms of insulin. Notably, the formulations can be used for both modified and un-modified insulin. In the case of un-modified insulin, one can avoid problems associated with using modified/analog insulin molecules such as irritation, immunogenic response, and costs.

These and other non-limiting aspects of the present invention are discussed below.

A. Insulin

Insulin helps the body use or store the blood glucose it gets from food. In people with type 1 diabetes, the pancreas no longer makes insulin. While people with type 2 diabetes make insulin, their bodies response to it is not efficient or not adequate, which is oftentimes referred to as insulin resistance.

Insulin itself is a peptide hormone that is well-known and characterized. The monomeric form of human insulin is composed of 51 amino acids, which is further characterized into two peptide chains referred to as the A chain and B chain that are coupled by disulfide bonds. In most species, the A chain consists of 21 amino acids and the B chain of 30 amino acids. Although the amino acid sequence of insulin varies among species, certain segments of the molecule are highly conserved. These similarities in the amino acid sequence of insulin lead to a three dimensional conformation of insulin that is very similar among species, and insulin from one animal can be biologically active in other species. For example, pig insulin has been widely used to treat human patients. The monomer form of insulin can associate together to form dimers. The dimers can associate together to form hexamers, which occurs typically in the presence of zinc.

Both of the monomer and dimer forms of insulin readily diffuse into blood. By comparison, hexamers diffuse poorly in large part due to their significantly greater size. As noted above, this has led to the production of modified insulin or insulin analogs (e.g., Lispro, Aspart, Glulisine, Detemir, Degludec, etc.), which are commercially available and useable in the context of the present invention. Further, regular non-modified insulin is also readily commercially available (e.g., HUMULIN® R, HUMULIN® N, HUMULIN® 70/30, NOVOLIN®, etc.) and also useable in the context of the present invention. In certain aspects, the regular/non-modified form of insulin can be used in lieu of the modified form so as to reduce allergic or immunogenic costs or to reduce the costs of the formulation. Insulin is currently produced by numerous manufacturers including pharmaceutical companies and contract drug manufacturers. Pharmaceutical manufacturers include Eli Lilly and Co., Novo Nordisk and Sanofi. Contract manufacturers include Sigma-Aldrich, Lonza, and Biocon. The insulin used in the Examples of this specification was recombinant non-modified human insulin purchased from Sigma-Aldrich (Saint Louis, Mo.).

B. pH Memory

The inventors also discovered a processing step that can be used to further stabilize the solubilized insulin within the formulation. This step includes mixing insulin with a non-volatile buffer in an aqueous solution and then drying the mixture to obtain dried insulin. Prior to drying, the aqueous solution has a pH range between 1 to 4 or between 6 to 8, which is the optimal pH ranges for insulin stability in an aqueous environment. Thus, once the mixture is dried, it produces a dried insulin having a "pH memory" between 1 to 4 or between 6 to 8, such that the pH memory remains after the dried insulin is solubilized within the aprotic polar solvent. In some particular instances when pramlintide is further included, the insulin pH memory can be about 2 and the pramlintide pH memory can be about 2.

In particular, the "pH memory" of insulin is the resulting charge profile (protonation state) after drying insulin from a buffered aqueous solution (e.g. from a non-volatile buffer). The protonation state, and thus the solubility and stability of insulin in aprotic polar solvents is affected by the pH of the aqueous insulin mixture or solution prior to drying. When insulin is dried in a buffer species in which both the acidic and basic components are non-volatile, the pH memory of the dried insulin will be about equal to the pH of the aqueous insulin mixture or solution. See, e.g., *Enzymatic Reactions in Organic Media*, Koskinen, A. M. P., and Klibanov, A. M., eds., Springer (1996). Furthermore, the pH of the buffered aqueous solution (e.g., non-volatile buffer) in which the insulin is dried can be optimized to yield a pH memory for the insulin that results in optimal stability, maximum solubility, and minimal degradation when the dried insulin is subsequently reconstituted in the aprotic polar solvent. Therefore, when dried insulin is reconstituted into such a solvent, the insulin in the reconstituted formulation will maintain the solubility and stability characteristics of the optimal pH memory.

The pH memory of insulin can be measured in several ways. In one method, the pH memory is measured by reconstituting the dried insulin into un-buffered water and measuring the pH of the reconstituted insulin mixture or solution with a pH indicator such as pH paper or a calibrated pH electrode. Alternatively, the pH memory can be determined by adding at least 20% water to the insulin/aprotic polar solvent formulation and measuring the pH of the formulation with a pH indicator. See, e.g., Baughman and Kreevoy, "Determination of Acidity in 80% Dimethyl Sulfoxide-20% Water," *Journal a/Physical Chemistry,* 78(4):421-23 (1974). Measurement of pH in an aprotic polar solvent-water solution may require a small correction (i.e., no more than 0.2 pH unit as per Baughman and Kreevoy, supra).

In view of the above, non-volatile buffers that are useful in the formulations described herein are those that are helpful in establishing a pH of maximum stability/minimal degradation as well as those that are helpful in removing residual moisture or water content from the insulin. Nonvolatile buffers include those buffers that will not evaporate away in a manner similar to water upon drying/lyophilization. Suitable nonvolatile buffers include, for example, glycine buffers, citrate buffers, phosphate buffers, and the like. In particular instances, the nonvolatile buffer is a glycine buffer or a citrate buffer.

Drying of the insulin with the nonvolatile buffer can be carried out using spray-drying techniques, freeze-drying techniques, lyophilization techniques, vacuum centrifugation techniques, etc. Spray drying techniques are well known to those skilled in the art. Spray drying includes the steps of atomization of a solution containing one or more solids (e.g., therapeutic agent) via a nozzle spinning disk, or other device, followed by evaporation of the solvent from the droplets. The nature of the powder that results is the function of several variables including the initial solute concentration, size distribution of droplets produced and the rate of solute removal. The particles produced may comprise aggregates of primary particles which consist of crystals and/or amorphous solids depending on the rate and conditions of solvent removal. A spray-drying process for preparing ultra-fine powders of drugs is described, for example, in U.S. Pat. No. 6,051,256. Freeze-drying procedures are well known in the art, and are described, for example, in U.S. Pat. No. 4,608,764 and U.S. Pat. No. 4,848,094. Spray-freeze-drying processes are described, for example, in U.S. Pat. No. 5,208,998. Other spray-drying techniques are described, in U.S. Pat. Nos. 6,253,463; 6,001,336; 5,260,306; and PCT International Publication Nos. WO91/16882 and WO 96/09814.

Lyophilization techniques are well known to those skilled in the art. Lyophilization is a dehydration technique that takes place while a product is in a frozen state and under a vacuum (ice sublimation under a vacuum) and drying by gentle heating. These conditions stabilize the product, and minimize oxidation and other degradation processes. The conditions of freeze drying permit running the process at low temperatures, therefore, thermally labile products can be preserved. Steps in freeze drying include pretreatment, freezing, primary drying and secondary drying. Pretreatment includes any method of treating the product prior to freezing. This may include concentrating the product, formulation revision (i.e., addition of components to increase stability and/or improve processing), decreasing a high vapor pressure solvent or increasing the surface area. Methods of pretreatment include: freeze concentration, solution phase concentration, and formulating specifically to preserve product appearance or to provide lyoprotection for reactive products, and are described, e.g., in U.S. Pat. No. 6,199,297. "Standard" lyophilization conditions, are described, e.g., in U.S. Pat. No. 5,031,336, and in "Freeze Drying of Pharmaceuticals" (DeLuca, Patrick P., J. Vac. Sci. Technol., Vol. 14, No. 1, January/February 1977); and "The Lyophilization of Pharmaceuticals: A Literature Review" (Williams, N. A., and G. P. Polli, Journal of Parenteral Science and Technology, Vol. 38, No. 2, March/April 1984).

In certain aspects, the lyophilization cycle can be partially performed above the glass transition temperature (Tg) of insulin to induce a collapse of the mass to form a dense cake containing residual moisture. In other embodiments, the lyophilization cycle is carried out below the glass transition temperature of insulin in order to avoid a collapse in order to achieve a complete drying of the insulin particles.

C. Aprotic Polar Solvent

After the dried insulin having its selected pH memory is obtained, the dried insulin can then be reconstituted and solubilized into an aprotic polar solvent. Aprotic polar solvents include those solvents that lack an acidic hydrogen. This feature is helpful in maintaining the pH memory of the dried insulin. Non-limiting examples of aprotic polar solvents include dimethylsulfoxide (DMSO), dimethylformamide (DMF), ethyl acetate, n-methyl pyrrolidone (NMP), dimethylacetamide (DMA), propylene carbonate, and mixtures thereof. Each of these solvents are well-known and commercially available from a wide variety of sources.

As shown in the examples, the solubilized insulin results in stable monomeric and dimeric forms of insulin, which can result in a ultra-fast or rapid acting insulin product. Further, and as noted above, and without wishing to be bound by theory, it is believed that the solubilized insulin is "metastable" in the aprotic polar solvent. It is thought that this meta-stability is derived from the combination of the insulin's pH memory and the solubility of the insulin within the aprotic polar solvent.

D. Ingredients to Reduce Aggregation of Insulin

Additional ingredients can be added to the formulation that further reduce the likelihood of aggregation of the monomeric and/or dimeric forms of insulin. These ingredients can be used to reduce such aggregation within the formulation prior to administration (e.g., during storage) or post administration (e.g., after administration and prior to absorption into a subject's blood stream). Such ingredients that can be used include urea, guanidinium chloride, amino acids, sugars, polyols, polymers, acids, surfactants, or mixtures thereof. Such ingredients are commercially available from a wide variety of sources.

E. Water Content of Formulations

The formulations of the present invention can have a low moisture or water content by virtue of using relatively high amounts of the aprotic polar solvents. This can provide additional stability for the monomeric and dimeric forms of insulin present within the formulations by reducing the likelihood of aggregation of said monomers and dimers. For instance, the formulations of the present invention can have a moisture or water content that is 20%, 19%, 18% 17%, 16%, 15%, 10%, 9%, 8%, 7%, 6%, 5%, 4%, 3%, 2%, 1%, 0.5%, 0.25%, 0.1%, 0.05%, 0.025%, 0.01%, to 0% by weight or volume of the formulation. In some instances, however, water can also be used as a co-solvent, such as when the formulation of the present invention includes insulin and pramlintide.

F. Insulin/Pramlintide Co-Formulations

Amylin, a β-cell hormone that is normally co-secreted with insulin in response to glucose intake, is also completely deficient in patients with Type 1 diabetes mellitus. Amylin exhibits several glucoregulatory effects that complement those of insulin in postprandial glucose regulation. Native human amylin is unsuitable for clinical or pharmaceutical use because of several physicochemical properties, including poor solubility, self-aggregation, and formation of amyloid fibrils, and amyloid plaques.

Pramlintide is an analog of human amylin developed by selectively substituting proline for Ala-25, Ser-28, and Ser-29. It addresses the suboptimal physicochemical properties of human amylin while preserving the important metabolic actions. Pramlintide is widely available from several commercial sources (e.g., SYMLIN® from Amylin Pharmaceuticals).

Pramlintide is typically administered via separate subcutaneous injections in addition to insulin. This practice is accepted by some sub-population of patients, but taking additional injections creates a significant burden on patients already injecting insulin multiple times daily. Also, it is possible that some patients might either inadvertently or deliberately mix pramlintide and insulin in the same syringe before injection, leading to adverse or undesirable events.

One of the reasons for separate administrations of pramlintide and insulin is that these drugs conflict in their buffering systems, making compatibility of a mixed formulation difficult. For instance, several insulins and insulin analogs have an isoelectric point in the range of 5-6 and are thus formulated at a pH of around 7. Pramlintide has an isoelectric point of >10.5, is optimally stable at a low pH, and is formulated at a pH typically around 4. The interaction of pramlintide and insulin formulations at different pHs and different buffering capacities often results in precipitation of soluble insulin components or solubilization of crystalline insulin components. In vitro studies with pramlintide and short- and long-acting insulin formulations found substantial variability in insulin solubility when various quantities of insulin were mixed with fixed quantities of pramlintide.

These problems co-formulation issues are solved by the present invention. For instance, the pramlintide can be dried in a buffer system such that it has a pH memory between 1 to 5, or 2, 3, or 4, or more particularly around 2. The insulin can be dried in the same or a separate buffer system such that it has a pH memory of around 1 to 4, 1 to 3, or around 2 or 6 to 8 or around 7. The dried pramlintide and insulin can then be reconstituted and solubilized within the same aprotic polar solvent and maintain their respective solubility and stability features within the same formulation. As such, only a single formulation is needed to administer both pramlintide and insulin to a subject. Such a co-formulation would lower the resistance of subjects to a therapy that more closely mimics the natural physiological response to post-prandial rise in blood glucose levels. In some particular instances of the co-formulation, the insulin pH memory can be about 2 and the pramlintide pH memory can be about 2.

In addition to pramlintide, other amylin agonists can be used in the context of the present invention. Such agonists can be recombinant or purified from a natural source. The amylin agonists can be human or non-human. The amylin agonist may also be an amylin analog which may be based on the amino acid sequence of human amylin but having one or more amino acid differences, or a chemically modified amylin or amylin analog. The dosages of the amylin agonist depend on its bioavailability and the patient to be treated. "Human amylin" includes the human peptide hormone secreted by the pancreas, whether isolated from a natural source, prepared through synthetic peptide chemistry or made by genetically altered microorganisms. "amylin analog" is an altered amylin, different from the amylin secreted by the pancreas, but still available to the body for performing the same action as natural amylin.

G. Dosages

Any suitable dosage of insulin, pramlintide, or combination of both can be administered using the formulations of the present invention. The dosage administered will, of course, vary depending upon known factors, such as: the pharmacodynamic characteristics of the particular drug, salt, or combination thereof; the age, health, or weight of the subject; the nature and extent of symptoms; the metabolic characteristics of the therapeutic agent and patient, the kind of concurrent treatment; the frequency of treatment; or the effect desired. Generally, insulin can be present in the formulation in an amount ranging from about 0.5 mg/mL to about 100 mg/mL. In some embodiments, the insulin is present in the formulation in an amount ranging from about 3 mg/mL to about 100 mg/mL, 3 mg/mL to about 10 mg/mL, 10 mg/mL to about 50 mg/mL, or from about 50 mg/mL to about 100 mg/mL. In certain aspects, the amount of insulin with the formulation ranges from about 3 mg/mL to about 10 mg/mL, which can result in a significant portion of the insulin being present in monomeric form (see data in Examples). In other instances, the amount of insulin with the formulation ranges from about 10 mg/mL to about 50 mg/mL, which can result in a majority of the insulin being present in dimeric form (see data in Examples). In some embodiments, the pramlintide is present in the formulation in an amount ranging from 0.1 to 10 mg/mL, or 0.2, 0.3, 0.4, 0.5, 0.6, 0.7, 0.8, 0.9, 1, 2, 3, 4, 5, 6, 7, 8, or 9 mg/mL or as needed. Again, it will be readily apparent to those of skill that the drug dosage can be varied depending on the drug used and the disease, disorder or condition to be treated, and the concentration of the drug in the formulation will vary depending on the drug solubility, dosage, and method of administration.

H. Additional Ingredients/Pharmaceutical Excipients

The formulations of the present invention can include additional ingredients/pharmaceutical excipients to further develop a formula to have a desired tactile property, viscosity range, or to further protect the insulin or pramlintide. For instance, the formulations can further include any one of, any combination of, or all of an antioxidant (non-limiting examples of which include ascorbic acid, cysteine, methionine, monothioglycerol, sodium thiosulfate, sulfites, BHT, BHA, ascorbyl palmitate, propyl gallate, or vitamin E or any combination thereof); a chelating agent (non-limiting examples of which include EDTA, EGTA, tartaric acid and salts thereof, glycerin, and citric acid and salts thereof); and/ or a preservative (non-limiting examples of which include alkyl alcohols, benzyl alcohols, methyl parabens, propyl parabens and mixtures thereof). Further, the formulations of the present invention can also include a non-aqueous protic solvent (non-limiting examples of which include polyethylene glycol (PEG), propylene glycol (PG), polyvinylpyrrolidone (PVP), methoxypolyethylene glycol (MPEG), glycerol, glycofurol, and mixtures thereof).

I. Kits/Containers

Kits are also contemplated as being used in certain aspects of the present invention. For instance, a formulation of the present invention can be included within a kit. A kit can include a container. In one aspect, for instance, the formulation can be comprised within a container that is ready to parenterally administer to a subject without having to reconstitute or dilute the formulation. That is, the formulation to be administered can be stored in the container and be readily used as needed. The storage container can be a syringe, a pen injection device, an auto-injector device or a pump. Suitable pen/auto-injector devices include, but are not limited to, those pen/auto-injection devices manufactured by Becton-Dickenson, Swedish Healthcare Limited (SHL Group), YpsoMed Ag, and the like. Suitable pump devices include, but are not limited to, those pump devices manufactured by Tandem Diabetes Care, Inc., Delsys Pharmaceuticals and the like.

Alternatively, a kit of the present invention can include multiple containers or multiple compartments within a container. Each container or multiple compartments can be used to store, for instance, the biocompatible non-aqueous solvent and the small molecule drug separately. Then, as needed, the solvent and drug can be mixed together and administered immediately or stored for a later time, as needed.

J. Method of Making Formulation

Formulations of the present invention can be made by using the following steps. These steps were used to make the formulations in the Examples of the specification.

1. Aqueous insulin is prepared by dissolving insulin powder (e.g., recombinant human insulin, Sigma-Aldrich, Saint Louis, Mo.) in the desired aqueous buffer (comprising specific buffer species, concentration and pH; e.g., citrate, pH 2.0) at an insulin concentration of 10 mg/mL.
2. Pramlintide (e.g., AmbioPharm, Inc., Beech Island, S.C. and C S Bio, Inc., Menlo Park, Calif., which was used in the Examples of the specification) can be prepared similarly, except pramlintide can be dissolved in aqueous buffer at a concentration of 2 mg/mL.
3a. The insulin or pramlintide solution is dispensed into clear HPLC or lyophilization vials and lyophilized according to the following or similar lyophilization cycle in Table 1.

TABLE 1

| Step | Temperature Condition | Rate/ Duration | Vacuum (mTorr) |
|---|---|---|---|
| Shelf load | 5° C. | 1 hr | N/A |
| Freezing | −50° C. | 1° C./min | N/A |
| Freeze Soak | −50° C. | 2 hrs | N/A |
| Ramp to Annealing | −15° C. | 1° C./min | N/A |
| Annealing | −15° C. | 1 hrs | N/A |
| Primary Drying | −15° C. | 24 hrs | 100 |
| Ramp to Secondary | 25° C. | 1° C./min | 100 |
| Secondary Drying | 25° C. | 8 hrs | 100 |
| Stoppering | 25° C. |  | 100 |

3b. Alternatively, aqueous insulin or pramlintide solution is dispensed into microcentrifuge tubes and dried by centrifugation under vacuum and gentle heat (25-30° C.).
4. Dried insulin or pramlintide powder at the selected pH memory is dissolved in DMSO by gentle pipetting to the desired concentration, or the concentration permitted by the particular buffer system and pH.
5. The resulting solutions are assessed visually for clarity and/or analyzed for light scattering using visible spectroscopy at 630 nM, and used in various downstream applications.

EXAMPLES

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

This example provides information on how to prepare insulin/DMSO formulations, in which the insulin has a pH memory of around 2. Comparative insulin/$H_2O$ formulations are also provided and used for Fourier-Transform Infrared Spectroscopic (FTIR) and Dynamic Light Scattering (DLS) analysis (discussed below in Examples 2 and 3, respectively). Note that the insulin used in the Examples of this specification was recombinant non-modified human insulin purchased from Sigma-Aldrich (Saint Louis, Mo.).

Insulin/Buffer A/DMSO:

Recombinant human insulin (Sigma-Aldrich, Saint Louis, Mo.) was dissolved at a concentration of 10 mg/mL in buffer A (i.e., 10 mM citrate+1 mM EDTA, pH 2.0), dispensed into HPLC vials in 0.25 mL-aliquots, and lyophilized according to the procedure outlined in steps 1-5 above in the "Method of Making Formulation" section. The lyophilized insulin in each vial had a pH memory of 2.0 and was reconstituted with 100 μL of DMSO to a concentration of 25 mg/mL (insulin was solubilized in DMSO per visual inspection). Aliquots of this stock were then further diluted with buffer A to create citrate-buffered insulin/DMSO/$H_2O$ solutions as desired (e.g., 12.5 and 5 mg/mL of insulin in DMSO and buffer A). These formulations are referred to as "Ins-A/DMSO" or indicated dilutions thereof.

Insulin/Buffer A/$H_2O$:

Insulin was dissolved at a concentration of 10 mg/mL in distilled, deionized water and lyophilized in 0.25 mL aliquots. The source of insulin and the lyophilization procedures were the same as those described above. Vials were reconstituted with 250 μL of buffer A (i.e., $H_2O$+10 mM citrate+1 mM EDTA, pH 2.0), which produced an insulin in buffer A solution at 10 mg/mL. Aliquots of this stock were then further diluted with buffer A to create insulin/buffer A solutions as desired (e.g., 5 mg/mL of insulin in buffer A). The insulin was solubilized in buffer A per visual inspection. These formulations are referred to as "Ins-A/$H_2O$."

Insulin/Buffer E/DMSO:

Insulin was dissolved at a concentration of 10 mg/mL in buffer E (i.e., $H_2O$+10 mM citrate+1 mM EDTA+10 mM NaCl, pH 2.0) and lyophilized in 0.5 mL aliquots. The source of insulin and the lyophilization procedures were the same as those described above. The lyophilized insulin in each vial had a pH memory of 2.0, and was reconstituted with 100 μL of DMSO to a concentration of 50 mg/mL. Insulin was solubilized in DMSO per visual inspection. Aliquots of this stock were then further diluted with DMSO to create insulin/DMSO solutions as desired (e.g., 30, 25, 10, 5, and 3 mg/mL of insulin in DMSO). These formulations are referred to as "Ins-E/DMSO."

Insulin/Buffer E and F/H$_2$O:

Insulin was dissolved at a concentration of 10 mg/mL in distilled, deionized water, and lyophilized in 0.5 mL aliquots. The source of insulin and the lyophilization procedures were the same as those described above. One vial was reconstituted with 500 µL of buffer E, which produced an insulin in buffer E solution at 10 mg/mL. The other vial was reconstituted with 500 µL of buffer F (i.e., H$_2$O+10 mM phosphate-citrate+1 mM EDTA+10 mM NaCl, pH 7.0), which produced an insulin in buffer F solution at 10 mg/mL. The insulin was solubilized in both the buffer E and F solutions per visual inspection. These samples are referred to as "Ins-E/H$_2$O" and "Ins-F/H$_2$O," respectively.

Example 2

This example provides FTIR data showing the effects of DMSO on insulin conformation. BioTools Inc. (Jupiter, Fla. USA) performed the FTIR analysis and provided corresponding data (see below).

Materials and Methods for FTIR Analysis:

The following formulations were prepared for the FTIR analysis:

Formula 1 (F1): Ins-A/DMSO diluted with 1 part buffer A to 12.5 mg/mL.
Formula 2 (F2): Ins-A/H$_2$O diluted to 5 mg/mL with buffer A.
Formula 3 (F3): Ins-A/H$_2$O reconstituted to 10 mg/mL with buffer A.
Formula 4 (F4): Ins-A/DMSO at 25 mg/mL.
Formula 5 (F5): Ins-A/DMSO diluted with 4 parts buffer A to 5 mg/mL.

FTIR spectra were collected on PROTA FTIR spectrometer (BioTools, Inc) equipped with DTGS detector at 4 cm-1 resolution with collection time of 20 minutes for each sample and buffer. Samples were dissolved as described, and placed in 6 um BioCell with CaF2 windows for water-based samples and 75-microns for DMSO-based samples. All spectral analysis (buffer subtraction and structure elucidation) was performed using the PROTA software suite.

Results:

FIG. 1 shows the FTIR spectra in the conformation-sensitive amide 1 region. These data confirm that insulin does not irreversibly unfold in DMSO, as the insulin profile remains relatively constant over the formulas 1-5 that were tested. Notably, formula 3 shows the typical insulin spectrum indicative of a mixed α-helix, β-sheet protein. Formula 4 shows a shift to a higher frequency while retaining its profile. This may be the result of a conformational change or the stronger hydrogen-bonding character of the DMSO solvent. Formula 5 is essentially identical to the aqueous spectrum of insulin. These data in FIG. 1 confirm that insulin does not irreversibly unfold in DMSO.

Example 3

This example provides DLS analysis to confirm the association state of insulin (i.e., monomeric form, dimeric form, hexameric form) in DMSO with comparison to control samples. Alliance Protein Laboratories (Thousand Oaks, Calif. USA) performed the DLS analysis and provided corresponding data (see below). Note that the buffer E and buffer F systems were used due to the presence of NaCl, which is needed to perform the DLS assay.

Materials and Methods for DLS Analysis:

The following formulations were prepared for the DLS analysis:

Formula 6 (F6): Ins-E/DMSO at 50 mg/mL.
Formula 7 (F7): Ins-E/DMSO at 30 mg/mL.
Formula 8 (F8): Ins-E/DMSO at 10 mg/mL.
Formula 9 (F9): Ins-E/DMSO at 3 mg/mL.
Formula 10 (F10): Ins-E/H$_2$O at 10 mg/mL.
Formula 11 (F11): Ins-F/H$_2$O at 10 mg/mL.

In DLS (also known as quasi-elastic light scattering or photon correlation spectroscopy) the time-dependent fluctuations in scattered light are measured. These fluctuations are related to the Brownian motion of the molecules, and therefore can be used to determine the diffusion coefficient. This diffusion coefficient is usually converted to the hydrodynamic (Stokes) radius, $R_h$, through the Stokes-Einstein relation:

$$R_h = k_\beta T / 6\pi\eta D$$

where $k_\beta$ is the Boltzmann constant, T is absolute temperature, $\eta$ is the solvent viscosity, and D is the diffusion coefficient.

Data were collected at a regulated temperature of 25° C. using a Protein Solutions (now Wyatt Technology) DynaPro MS/X instrument using 12 µL quartz scattering cells. Samples were centrifuged for 10 minutes in a microcentrifuge (Fisher model 235 A) to remove dust and large particulates prior to loading into the analysis cuvette. Typically 25 ten-second data accumulations were recorded and averaged to improve signal/noise. The resulting data were analyzed with the Dynamics version 6.12.0.3 software provided by the manufacturer. Mean (z-average) sizes are based on the cumulants method. Size distributions were calculated using the Dynals analysis method. Weight fractions were estimated using the Ralleigh spheres model. The instrument calibration is absolute, based on units of time and distance (with distance measured by the wavelength of the light source). However, that instrument calibration is confirmed annually using calibrated latex sphere size standards (diameter 21±1.5 nm, product 3020A lot 35266 from Thermo Scientific). The viscosity index of the DMSO were assigned as 1.991 cp and 1.4768.

Figure 2:
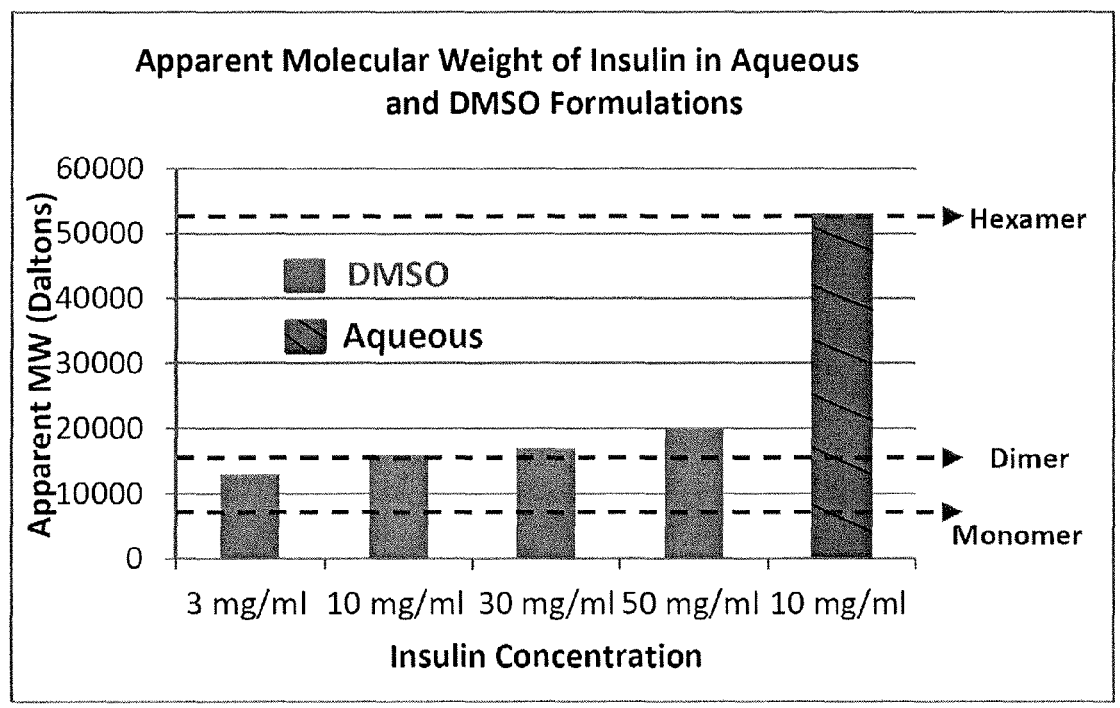
FIG. 2: Apparent molecular weight of DMSO/Insulin and Aqueous/Insulin formulations.

Overall Results:

The aggregation state of insulin in DMSO was examined using dynamic light scattering (DLS). Monomeric insulin has a true MW of approximately 6 kDa. Consequently, dimeric insulin would have a true MW of 12 kDa and hexameric insulin, 36 kDa. FIG. 2 summarizes the apparent molecular weight (MW) of insulin measured in the prepared DMSO and aqueous solutions (i.e., formulas 6-10). The apparent MW of insulin in an aqueous formulation at pH 7.0 and concentration of 10 mg/ml (formula 10) is 53 kDa. At this high concentration, the solution is likely non-ideal, with intermolecular effects resulting in an apparent MW that is larger than the true MW. Regardless, the measured apparent MW is indicative of insulin in a hexameric state.

With respect to the insulin/DMSO formulations, at 10 mg/ml (formula 7), the apparent MW is 16 kDa, approximately one-third the MW of aqueous insulin at 10 mg/ml (formula 10), indicating that insulin in DMSO associates as a dimer at this concentration. This also appears to be the case for concentrations up to 50 mg/ml (formulas 8-9), as the approximately linear difference in apparent MW observed with increasing concentration is likely an artifact of an excluded volume effect typical for this technique. However, the reduction in apparent MW to 13 kDa at 3 mg/ml (formula 6) deviates from this trend, and indicates that reversible dissociation to monomer exists at this concentration.

These DLS studies suggest that, over range of relevant use concentrations, the largest multimeric state of INS-2E in DMSO is a dimer, and at the lower end of the concentration range, a monomer-dimer equilibrium exists. These findings are in contrast to aqueous insulin formulations, where the hexamer predominates—even in the absence of zinc—and the monomer is unstable and rapidly fibrillates. Based on current kinetic models of insulin association and absorption, it is expected that an insulin formulation devoid of hexameric insulin should result in absorption kinetics more rapid than those of current rapid-acting insulins (e.g., Lispro®, Aspart®, etc.), which still contain significant quantities of hexameric insulin. Taken together, these physicochemical studies show that the approach of using a non-aqueous solvent to develop an ultra-rapid acting insulin formulation is more likely to be successful than an aqueous approach. In aqueous solution, including rapid-acting formulations, monomeric insulin is unstable and the hexameric form predominates, whereas in DMSO, the more rapidly absorbed insulin monomer/dimer is thermodynamically preferred, even at relatively high concentrations. Additionally, these data (including the DLS and FTIR data) show that any conformational change that appears to be induced by DMSO is reversible upon reconstitution into an aqueous medium.

Figure 3:
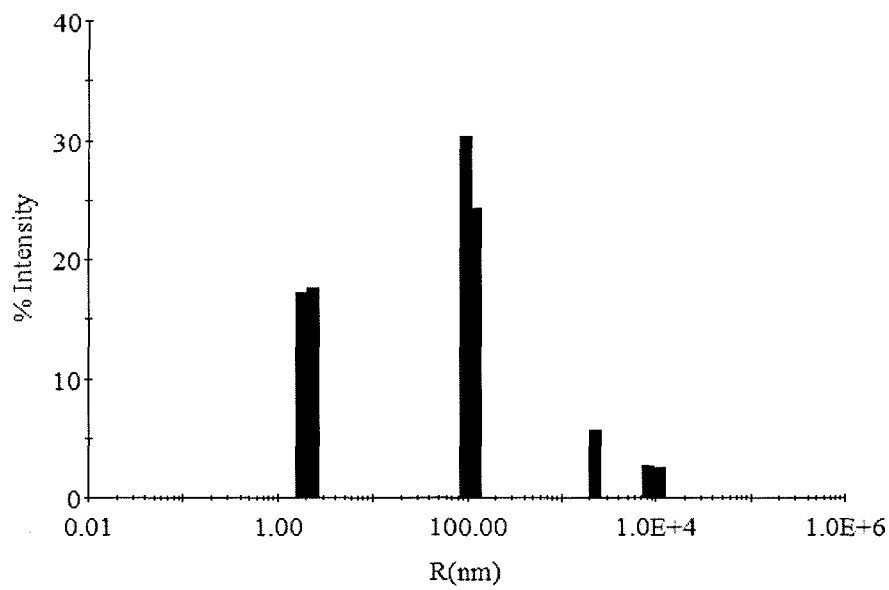
FIG. 3: Hydrodynamic radius distribution for Ins-E at 50 mg/mL in DMSO. The horizontal axis is a logarithmically-spaced grid of hydrodynamic radius values (with adjacent points differing by a factor of ~1.3). The analysis covers a range of radii from ~0.01 nm to ~20 µm. Peaks at 0.01-0.1 nm which are artifacts arising from after-pulsing of the photodetector have been suppressed.

Specific Results for Formula 6 (Ins-E/DMSO at 50 mg/mL):

The size distribution (histogram of scattering intensity vs. hydrodynamic radius) for Ins-E at 50 mg/mL in DMSO is shown in FIG. 3. The main peak (by weight) is the first peak, which has a mean radius of 2.12 nm and represents 34.7% of the total scattering intensity. That radius corresponds to a molar mass of roughly 20 kDa, based on aqueous globular protein standards. In addition to the main peak three peaks at larger radii are detected, at mean radii of 110 nm, 2.29 μm, and 9.85 μm. Although these 3 other peaks contribute about ⅔ of the total scattering intensity, they actually represent a very minor fraction on a percent by weight basis, as estimated in the Table 2 below. It is unfortunately not possible to make meaningful fraction by weight estimates for species larger than 1 μm because (1) the scattering from such large particles is very dependent on the detailed shape of the particle (due to internal reflections), and (2) nearly all the scattered light is emitted in the forward direction, with only a tiny fraction at the 90° angle observed here. Some or all of these other species might be due to contaminants or incompletely-dissolved buffer components rather than insulin aggregates.

TABLE 2*

(summary for Ins-E at 50 mg/ml in DMSO)

| Peak # | Mean Radius (nm) | Estimated Molar Mass | Fraction of Intensity | Fraction by Weight (%) |
|---|---|---|---|---|
| 1 | 2.12 | 20 kDA | 34.7 | 99.970 |
| 2 | 110 | 200 MDa | 54.5 | 0.030 |
| 3 | 2,290 | 250 GDa | 5.6 | ** |
| 4 | 9,850 | 7.4 TDa | 5.2 | ** |

*z-average radius 24.5 nm; mean intensity 182 kcnt/s.
** the weight fraction for species this large cannot be reliably estimated so this peak was excluded from this calculation.

Figure 4:
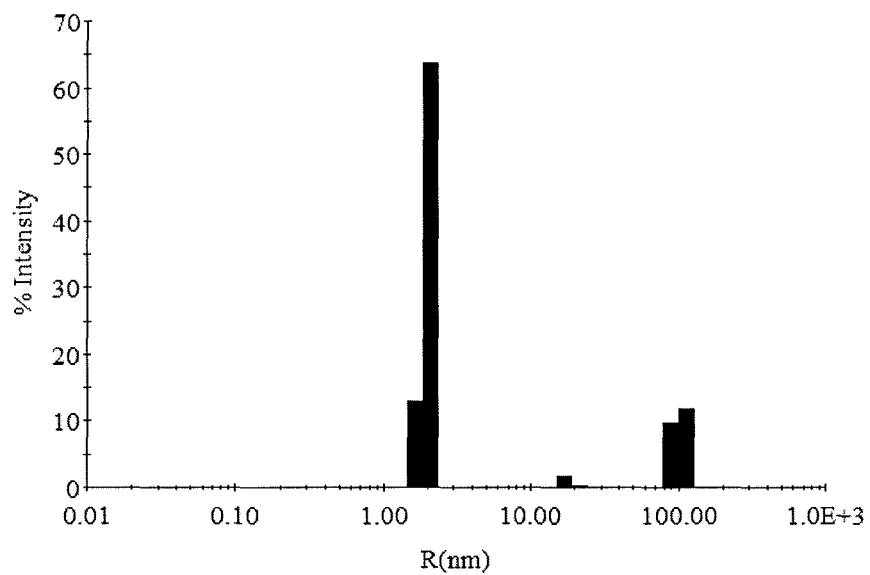
FIG. 4: Hydrodynamic radius distribution for Ins-E at 30 mg/mL in DMSO (see above FIG. 3 for graph explanation).

Specific Results for Formula 7 (Ins-E/DMSO at 30 mg/mL):

The size distribution obtained for INS-E at 30 mg/mL in DMSO is shown in FIG. 4. At this concentration the main peak has shifted to a slightly lower radius of 2.02 nm (estimated mass 17 kDa). Notably, the species at 2.29 and 9.85 μm are no longer detected, strongly suggesting that those were buffer components which have now dissolved. The relatively intensity of the species near 100 nm has also dropped substantially. At this concentration a new species at 17.7 nm was detected. Since that species represents only 1.9% of the total scattered light, it is possible that this species was present at the same level in the sample at 50 mg/mL, but was not detected because it was lost in the glare (the strong scattering from the species at 100 nm and larger). The raw data from DLS (the autocorrelation function) has a limited dynamic range, and that means that species which represent less than ~1% of the total scattered light often fall below detection threshold. A summary of these data is provided in Table 3 for formula 7.

TABLE 3*

(summary for Ins-E at 30 mg/ml in DMSO)

| Peak # | Mean Radius (nm) | Estimated Molar Mass | Fraction of Intensity | Fraction by Weight (%) |
|---|---|---|---|---|
| 1 | 2.02 | 17 kDa | 76.7 | 99.9932 |
| 2 | 17.7 | 2.8 MDa | 1.9 | 0.0037 |
| 3 | 102 | 170 MDa | 21.4 | 0.0031 |

*z-average radius 2.12 nm; mean intensity 77.9 kcnt/s.

Figure 5:
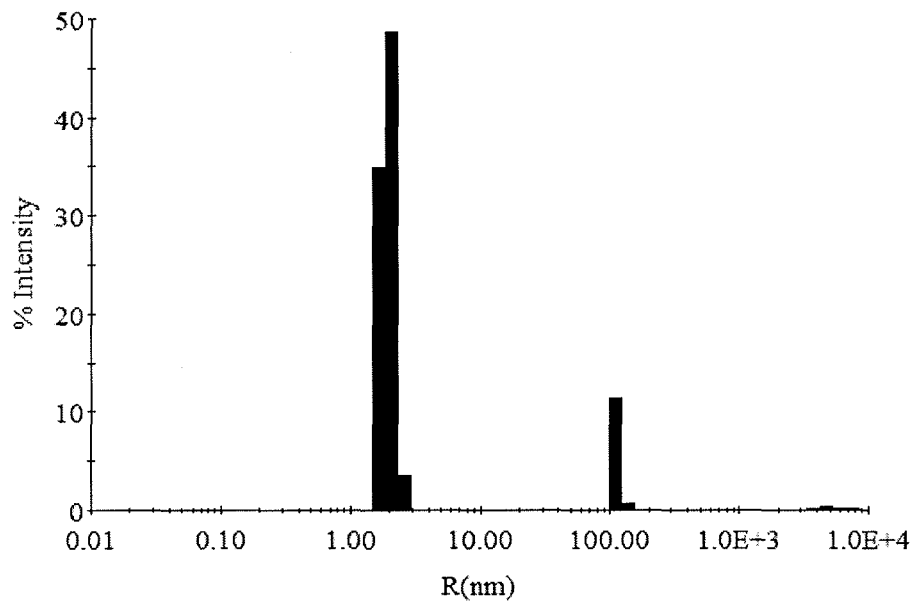
FIG. 5: Hydrodynamic radius distribution for Ins-E at 10 mg/mL in DMSO (see above FIG. 3 for graph explanation).

Specific Results for Formula 8 (Ins-E/DMSO at 10 mg/mL):

The size distribution at 10 mg/mL in DMSO is shown in FIG. 5. The dilution has further shifted the main peak down to 1.94 nm (estimated mass 16 kDa). At this concentration the peak at 17.7 nm was not detected, and the relative intensity of the species near 100 nm has dropped further. A trace of large particles at 5.45 μm was also present (but the removal of such species by the centrifugation is sometimes not complete). Table 4 provides a summary of the data for Formula 8:

TABLE 4*

(summary for Ins-E at 10 mg/ml in DMSO)

| Peak # | Mean Radius (nm) | Estimated Molar Mass | Fraction of Intensity | Fraction by Weight (%) |
|---|---|---|---|---|
| 1 | 1.94 | 16 kDa | 87.1 | 99.9975 |
| 2 | 115 | 220 kDa | 12.2 | 0.0025 |
| 3 | 5450 | 1.9 TDa | 0.7 | ** |

*z-average radius 1.07 nm; mean intensity 43.1 kcnt/s.
** the weight fraction for species this large cannot be reliably estimated so this peak was excluded from this calculation.

Figure 6:
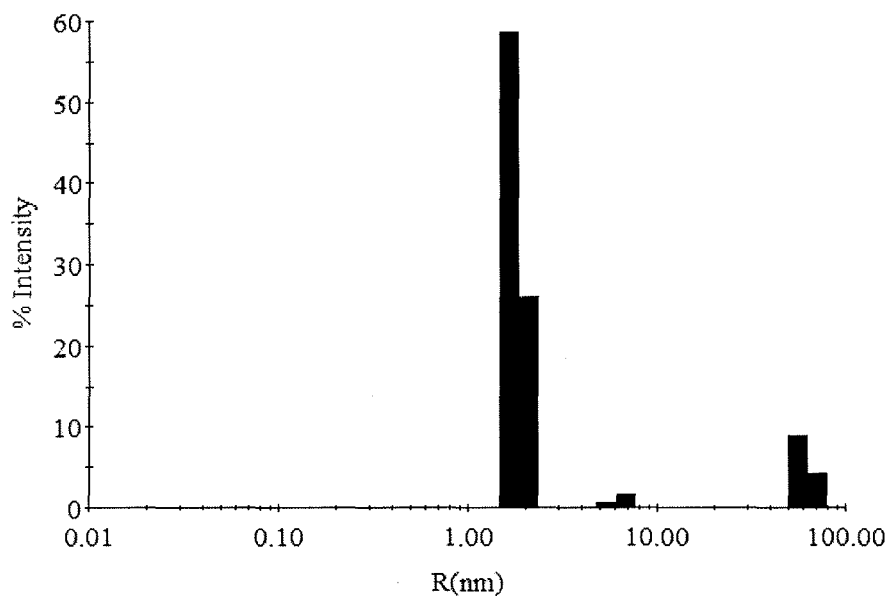
FIG. 6: Hydrodynamic radius distribution for Ins-E at 3 mg/mL in DMSO (see above FIG. 3 for graph explanation).

Specific Results for Formula 9 (Ins-E/DMSO at 3 mg/mL):

The size distribution at 3 mg/mL in DMSO is shown in FIG. 6. At this concentration the main peak falls at 1.79 nm (estimated mass 13 kDa). At this concentration a new peak at 6.34 nm was detected, which may represent a small amount of insulin aggregates (perhaps generated by the lyophilization). The peak seen in this sample at 60.8 nm is probably the same material measured as 100-110 nm at the higher concentrations—the apparent shift could be due either to the lower signal/noise at this concentration, or might be a consequence of resolving the new peak at 6.34 nm. Table 5 provides a summary of the data for Formula 9.

TABLE 5*

(summary for Ins-E at 3 mg/ml in DMSO)

| Peak # | Mean Radius (nm) | Estimated Molar Mass | Fraction of Intensity | Fraction by Weight (%) |
|---|---|---|---|---|
| 1 | 1.79 | 13 kDa | 84.7 | 99.9393 |
| 2 | 6.34 | 250 kDa | 2.2 | 0.060 |
| 3 | 60.8 | 50 MDa | 13.1 | 0.0009 |

*z-average radius 0.24 nm; mean intensity 31.4 kcnt/s.

Figure 7:
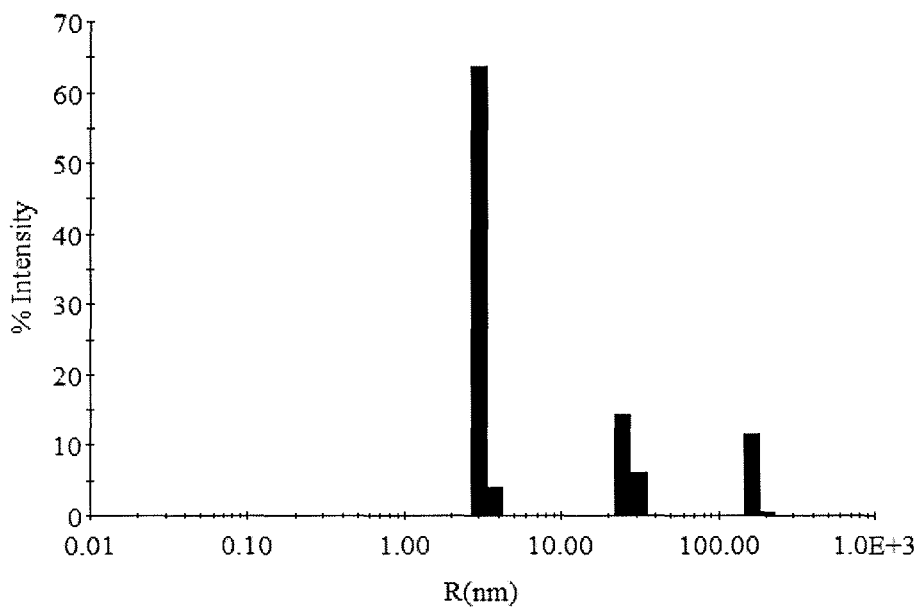
FIG. 7: Hydrodynamic radius distribution for Ins-$H_2O$ at 10 mg/mL in buffer E (see above FIG. 3 for graph explanation).

Specific Results for Formula 10 (Ins-E/H$_2$O):

The size distribution for Ins-H$_2$O in buffer E (pH 2.0) is shown in FIG. 7. The main peak occurs at a radius of 3.08 nm. That radius corresponds to an estimated mass of 47 kDa, suggesting the sample is still predominantly hexamer (or more) at this low pH. Note that at a concentration of 10 mg/mL the solution non-ideality ("molecular crowding") effects may be causing some distortion of the size, but whether that distortion would be upward or downward depends on whether the electrostatic or excluded volume effects dominate. Traces of larger species at 27 nm and 165 nm were also detected, but whether these represent insulin aggregates or particulate contaminants is unclear. Table 6 provides a summary of the data for Formula 10.

TABLE 6*

(summary for Ins-H$_2$O at 10 mg/ml in buffer E)

| Peak # | Mean Radius (nm) | Estimated Molar Mass | Fraction of Intensity | Fraction by Weight (%) |
|---|---|---|---|---|
| 1 | 3.08 | 47 kDa | 67.5 | 99.894 |
| 2 | 27.0 | 7.5 MDa | 20.5 | 0.053 |
| 3 | 165 | 520 MDa | 12.0 | 0.053 |

*z-average radius 4.06 nm; mean intensity 375 kcnt/s.

Figure 8:
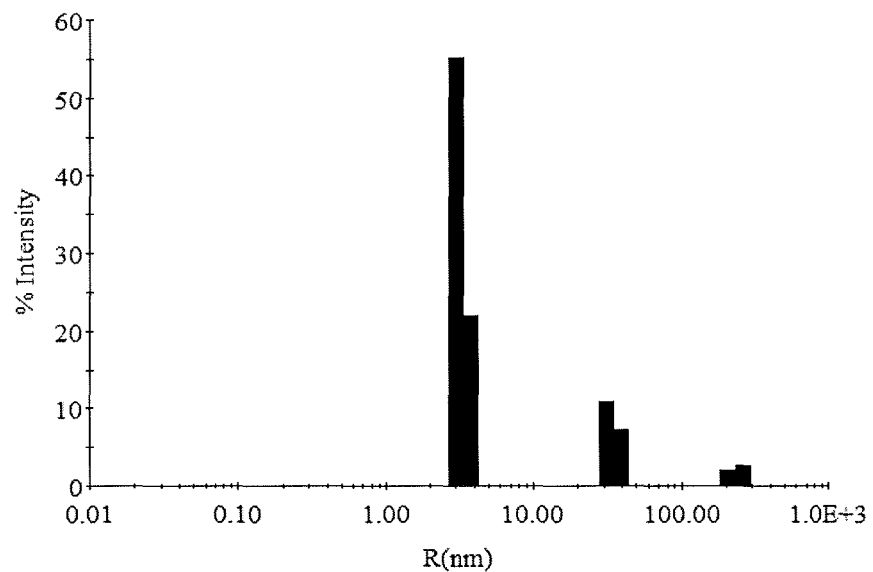
FIG. 8: Hydrodynamic radius distribution for Ins-$H_2O$ at 10 mg/mL in buffer F (see above FIG. 3 for graph explanation).

Specific Results for Formula 10 (Ins-F/H$_2$O):

The size distribution for Ins-H$_2$O in buffer F (pH 7.0) is shown in FIG. 8. The main peak occurs at a radius of 3.26 nm. That radius corresponds to an estimated mass of 53 kDa. Here again at 10 mg/mL the solution non-ideality effects may be causing some distortion of the size, but the lower charge at neutral pH would likely mean that excluded volume dominates and therefore the apparent size would be slightly larger than the true size. Traces of larger species at 35 nm and 238 nm were also detected. Table 7 provides a summary of the data for Formula 11.

TABLE 7*

(summary for Ins-H$_2$O at 10 mg/ml in buffer F)

| Peak # | Mean Radius (nm) | Estimated Molar Mass | Fraction of Intensity | Fraction by Weight (%) |
|---|---|---|---|---|
| 1 | 3.26 | 53 kDa | 77.2 | 99.9688 |
| 2 | 35.0 | 14 MDa | 18.2 | 0.023 |
| 3 | 238 | 1.2 GDa | 4.6 | 0.0078 |

*z-average radius 3.80 nm; mean intensity 447 kcnt/s.

Example 4

This example provides data concerning pramlintide and insulin/pramlintide co-formulations in the context of the formulations of the present invention.

Pramlintide Solubility in DMSO and DMSO-Water Co-solvents:

Solutions of pramlintide were prepared at a concentration of 2 mg/mL in 10 mM citrate, pH 2.0, or 10 mM citrate, pH 4.0, each with or without 2 mg/mL trehalose. The solutions were dried by centrifugation under vacuum for approximately 3.5 hours at 25-30° C., or lyophilized as described above.

Dried citrate-buffered pramlintide with a pH memory of 2.0 (with and without trehalose) completely dissolved in neat DMSO over several minutes with intermittent gentle pipetting at 20 mg/mL (the highest concentration tested). The resulting solution was flowable and completely clear by visual inspection.

Dried citrate-buffered pramlintide with a pH memory of 4.0 was somewhat resistant to reconstitution to the starting concentration of 2 mg/mL in neat DMSO, and was effectively insoluble in water. The addition of between 6% and 10% water to pramlintide in DMSO at nominal pramlintide concentrations between 2 and 5 mg/mL resulted in improved or nearly complete solubility of the peptide as measured by visual inspection.

Co-Formulation of Insulin and Pramlintide:

A co-formulation of insulin and pramlintide was prepared as follows: recombinant human insulin was dissolved at a concentration of 10 mg/ml in 10 mM citrate/1.0 mM EDTA buffer, pH 2. Pramlintide was dissolved at a concentration of 2 mg/mL in 10 mM citrate, pH 2.0, with or without 2 mg/mL trehalose. The solutions were dried by centrifugation under vacuum in 0.5-mL aliquots as described above. Insulin was reconstituted with 50 μL DMSO to a concentration of 100 mg/mL, and pramlintide was reconstituted with 50 μL DMSO to concentration of 20 mg/mL. Equal volumes of the peptide-DMSO solutions were mixed to yield a combined solution of 50 mg/ml insulin and 10 mg/mL pramlintide, with or without 10 mg/mL trehalose. The solutions were flowable and completely clear by visual inspection. The ratio of 5:1 (w/w) insulin:pramlintide is one possible representative therapeutic dosing ratio, and the peptides were maintained stably in a single, highly concentrated solution over 6 hours of visual observation. With pre-existing formulation technology, these peptides require separate and incompatible buffer systems, which in turn require administration via separate injections at separate sites on the body—a significant barrier to implementation of this beneficial treatment.

Example 5

This is a prophetic example to determine the bioactivity, pharmacological, and pharmacokinetic abilities of the formulations of the present invention when compared against existing rapid-acting insulin products (e.g., Aspart, Glulisine, Lispro).

Bioactivity:

Insulin action at the cellular level involves binding to the insulin receptor (IR), receptor autophosphorylation, IR-mediated phosphorylation of insulin receptor substrates, and subsequent activation of the PI3 kinase-Akt cascade. Receptor binding is determined, in part, by the association state of the insulin molecule, and thus can be a measure not only of the overall bioactivity of an insulin formulation, but also the multi- (or mono-) meric state of the peptide. Bioactivity of the formulations of the present invention can be measured and compared by their ability to induce IR phosphorylation in mouse embryo fibroblasts that over-express the IR-B isoform (the major version found in insulin-sensitive tissues), using an enzyme-linked immunosorbent assay (ELISA) kit from R&D Systems. As IR binding alone does not necessarily predict downstream signaling more proximal to the ultimate biological response, such as glucose regulation and fatty acid uptake and lipolysis, cell lysates can be similarly quantitated for phosphorylated Akt (see Marks, A. G., et al. (2011), "Plasma distribution and signaling activities of IGF-II precursors. Endocrinology," 152:922-930; Denley, A., et al. (2007), "Differential activation of insulin receptor substrates (IRS)-1 and 2 by IGF-activated insulin receptors," Mol. Cell. Biol. 27:3569-3577; and Denley, A., et al. (2006), "Differential activation of insulin receptor isoforms by insulin-like growth factors is determined by the C domain," Endocrinology, 147: 1029-1036, all of which are incorporated by reference).

Pharmacology:

Pharmacology studies can be carried out using an octreotide-infused conscious pig model with a subcutaneous indwelling vascular access port (VAP). The non-diabetic Yorkshire conscious pig model can be used on the basis of: (a) carbohydrate physiology similar to humans, (b) large veins suitable for IV catheter placement, (c) the conscious model obviates complications of prolonged anesthesia (atelectasis, pneumonia, difficult intubation/extubation), and (d) one pig can be used for multiple studies. The study can be designed to test formulations of the present invention having an acceptable insulin dose (e.g., 0.2 mg/kg) using time points 0, 5, 10, 20, 30, 45, 60, 90, 120, 180, and 240 minutes.

Pharmacokinetics:

Blood samples can be assayed using a previously validated assay for native and analog insulin in pig serum at OHSU (see MERCODIA® Iso-Insulin ELISA, Product number 10-1128-01, manufactured by Mercodia AB Uppsala, Sweden). Blood levels of human insulin (e.g., formulations of the present invention and a comparative aqueous formulation) as well as insulin analogs can be quantitated over the indicated time course and compared for area under the curve, Cmax, Tmax, early ½ Tmax and late ½ Tmax. The primary endpoints can be the early- and late ½ Tmax values, which are substantially more sensitive to changes in PK than Tmax. The Tmax often occurs on a long plateau, which can be difficult to measure and yield misleading results, whereas the early and late values rapidly rise and fall and are thus much more reliable.

All of the ingredients, compositions, or methods disclosed and claimed in this specification can be made and executed without undue experimentation in light of the present disclosure. While the ingredients, compositions, or methods of this invention have been described in terms of particular embodiments, it will be apparent to those of skill in the art that variations may be applied to the active ingredients, compositions, or methods and in the steps or in the sequence of steps of the method described herein without departing from the concept, spirit and scope of the invention.

The invention claimed is:

1. A formulation for parenteral administration comprising:
   (a) insulin that has a pH memory between 1 to 4 or between 6 to 8 and has been previously dried from a non-volatile buffer; and
   (b) an aprotic polar solvent,
   wherein the insulin is solubilized in the aprotic polar solvent, wherein the majority of the solubilized insulin is stable monomeric or dimeric forms of insulin or mixtures thereof, and
   wherein the water content of the formulation is equal to or less than 15% w/v.

2. The formulation of claim 1, wherein the pH memory of the insulin is between 1 to 4, or between 1 to 3, or about 2.

3. The formulation of claim 1, wherein the pH memory of the insulin is between 6 to 8, or about 7.

4. The formulation of claim 1, wherein the aprotic polar solvent is dimethylsulfoxide (DMSO), n-methyl pyrrolidone (NMP), ethyl acetate, dimethylformamide (DMF), dimethylacetamide (DMA), or propylene carbonate, or mixtures thereof.

5. The formulation of claim 4, wherein the aprotic polar solvent is dimethylsulfoxide (DMSO).

6. The formulation of claim 1, wherein the formulation comprises 3 mg/ml to 50 mg/ml, 3 mg/ml to 10 mg/ml, or 10 mg/ml to 50 mg/ml of insulin.

7. The formulation of claim 1, wherein the majority of the solubilized insulin is in monomeric form.

8. The formulation of claim 1, wherein the majority of the solubilized insulin is in dimeric form.

9. The formulation of claim 1, further comprising an aggregation inhibitor that reduces aggregation of monomeric or dimeric forms of insulin.

10. The formulation of claim 9, wherein the aggregation inhibitor is urea, guanidinium chloride, an amino acid, a sugar, a polyol, a polymer, an acid, a surfactant, or mixtures thereof.

11. The formulation of claim 10, wherein the acid is acetic acid, ascorbic acid, citric acid, glutamic acid, aspartic acid, succinic acid, fumaric acid, maleic acid, adipic acid, or mixtures thereof.

12. The formulation of claim 1, further comprising a co-solvent.

13. The formulation of claim 12, wherein the co-solvent is water.

14. The formulation of claim 1, wherein the formulation does not include zinc, or wherein zinc present in the formulation is bound to a chelating agent.

15. The formulation of claim 14, wherein the non-volatile buffer is a glycine buffer, a citrate buffer, a phosphate buffer, or mixtures thereof.

16. The formulation of claim 15, wherein the buffer further comprises a chelating agent.

17. The formulation of claim 14, wherein the chelating agent is ethylenediaminetetraacetic acid (EDTA), ethylene glycol tetraacetic acid (EGTA), tartaric acid, glycerin, or citric acid.

18. The formulation of claim 1, further comprising a freezing point depressant that depresses the freezing point of the aprotic polar solvent to about 0° C.

19. The formulation of claim 18, wherein the freezing point depressant is water, a sugar, a sugar alcohol, or mixtures thereof.

20. The formulation of claim 1, wherein the insulin is non-modified human insulin.

21. The formulation of claim 1, further comprising an amylin analog that is solubilized in the formulation.

22. The formulation of claim 21, wherein the amylin analog is pramlintide.

23. The formulation of claim 22, wherein the pramlintide has a pH memory of about 2, or wherein the pramlintide has a pH memory of about 2 and the insulin has a pH memory of about 2.

24. The formulation of claim 23, wherein the pramlintide has been previously dried in a non-volatile buffer having a pH of about 2.

25. The formulation of claim 22, wherein the water content of the formulation is between 5 to 15% w/v, between 7 to 12% w/v, between 8 to 10% w/v, or about 9% w/v.

26. The formulation of claim 1, wherein the formulation is in liquid form.

27. The formulation of 26, wherein the formulation is a solution.

28. The formulation of claim 1, wherein at least 90% of the insulin within the formulation remains chemically and physically stable when the formulation is stored at room temperature for one month.

29. The formulation of claim 1, wherein the formulation is in a container.

30. The formulation of claim 29, wherein the container is a syringe, a pen injection device, an auto-injector device, a pump, or a perfusion bag.

31. The formulation of claim 1, wherein the aprotic polar solvent is the continuous phase of the formulation.

32. The formulation of claim 1, wherein the formulation comprises at least 75, 80, 85, 90, or 95% w/v of the aprotic polar solvent.

33. The formulation of claim 1, wherein the solubilized insulin is meta-stable.

34. A method for reducing blood glucose level, comprising administering to a subject in need thereof a therapeutically effective amount of the formulation of claim 1 to reduce the blood glucose level in the subject.

\* \* \* \* \*